(12) United States Patent
Coelho Tsou et al.

(10) Patent No.: US 8,614,356 B2
(45) Date of Patent: Dec. 24, 2013

(54) METHOD FOR PRODUCING TOLUYLENEDIAMINE BY HYDROGENATING DINITROTOLUENE

(75) Inventors: Joana Coelho Tsou, Heidelberg (DE); Steffen Oehlenschlaeger, Antwerp (BE); Ekkehard Schwab, Neustadt (DE); Wolfgang Mackenroth, Tervuren (BE); Hartwig Voss, Frankenthal (DE); Stefan Maixner, Schwetzingen (DE); Samuel Neto, Dresden (DE); Sven Boehmeke, Senftenberg (DE); Frederik Van Laar, Maarssen (NL)

(73) Assignee: BASF SE, Ludwigshafen (DE)

( * ) Notice: Subject to any disclaimer, the term of this patent is extended or adjusted under 35 U.S.C. 154(b) by 100 days.

(21) Appl. No.: 13/142,718
(22) PCT Filed: Dec. 21, 2009
(86) PCT No.: PCT/EP2009/067610
§ 371 (c)(1), (2), (4) Date: Jun. 29, 2011
(87) PCT Pub. No.: WO2010/076251
PCT Pub. Date: Jul. 8, 2010

(65) Prior Publication Data
US 2011/0275858 A1   Nov. 10, 2011

(30) Foreign Application Priority Data
Dec. 29, 2008 (DE) .......................... 10 2008 063 308

(51) Int. Cl.
C07C 209/00 (2006.01)
C07C 211/00 (2006.01)

(52) U.S. Cl.
USPC ............ 564/422; 564/420; 564/415; 564/305

(58) Field of Classification Search
None
See application file for complete search history.

(56) References Cited

U.S. PATENT DOCUMENTS 2,976,320 A * 3/1961 Winstrom et al. ............ 564/423

(Continued)

FOREIGN PATENT DOCUMENTS

EP   0 124 010   11/1984

(Continued)

OTHER PUBLICATIONS

U.S. Appl. No. 13/109,399, filed May 17, 2011, Raichle, et al.

(Continued)

Primary Examiner — Clinton Brooks
(74) Attorney, Agent, or Firm — Oblon, Spivak, McClelland, Maier & Neustadt, L.L.P.

(57) ABSTRACT

A process for preparing tolylenediamine by hydrogenating dinitrotoluene with hydrogen in the presence of a suspended catalyst
  in a vertically upright reactor (1),
  at the upper end of which is arranged a motive jet nozzle (2) through which the reaction mixture drawn off from the reactor bottom, via an external loop, is sprayed into the upper region of the reactor (1) and then flows into a central inserted tube (4) which is arranged in the longitudinal direction of the reactor, flows through the latter from the top downward and flows upward again outside the inserted tube (4) in an internal loop motion,
  with a heat exchanger (6) in the interior of the reactor (1), through which cooling water flows, and absorbs some of the heat of reaction as it does so,
  with a feed for the dinitrotoluene at the upper end of the reactor (1) and a feed for the hydrogen at the lower end of the reactor (1),
  and wherein, in addition to the heat exchanger (6) arranged in the interior of the reactor (1), a further heat exchanger (W) is used in the external loop, in which water absorbs the rest of the heat of reaction by indirect heat exchange with the reaction mixture,
which comprises
utilizing the heat of reaction to raise steam with a pressure of at least 4 bar gauge by performing the hydrogenation of dinitrotoluene to tolylenediamine at a temperature of ≥180° C.

13 Claims, 1 Drawing Sheet

(56) References Cited

U.S. PATENT DOCUMENTS

| | | |
|---|---|---|
| 4,792,626 A | 12/1988 | Becher et al. |
| 5,563,296 A | 10/1996 | Zarnack et al. |
| 6,350,911 B1 | 2/2002 | Sander et al. |
| 2010/0130788 A1 | 5/2010 | Coelho Tsou et al. |
| 2010/0274008 A1 | 10/2010 | Kubanek et al. |
| 2010/0274009 A1 | 10/2010 | Kubanek et al. |
| 2010/0274010 A1 | 10/2010 | Kubanek et al. |
| 2010/0274011 A1 | 10/2010 | Kubanek et al. |
| 2010/0274055 A1 | 10/2010 | Kubanek et al. |
| 2011/0054167 A1 | 3/2011 | Kubanek et al. |
| 2011/0124933 A1 | 5/2011 | Kiesslich et al. |

FOREIGN PATENT DOCUMENTS

| | | |
|---|---|---|
| EP | 0 223 035 | 5/1987 |
| EP | 0 634 391 | 1/1995 |
| WO | 00 35852 | 6/2000 |
| WO | 2008 138833 | 11/2008 |
| WO | 2009 080515 | 7/2009 |

OTHER PUBLICATIONS

International Search Report issued Feb. 15, 2010 in PCT/EP09/067610 filed Dec. 21, 2009, 3 pages.

* cited by examiner

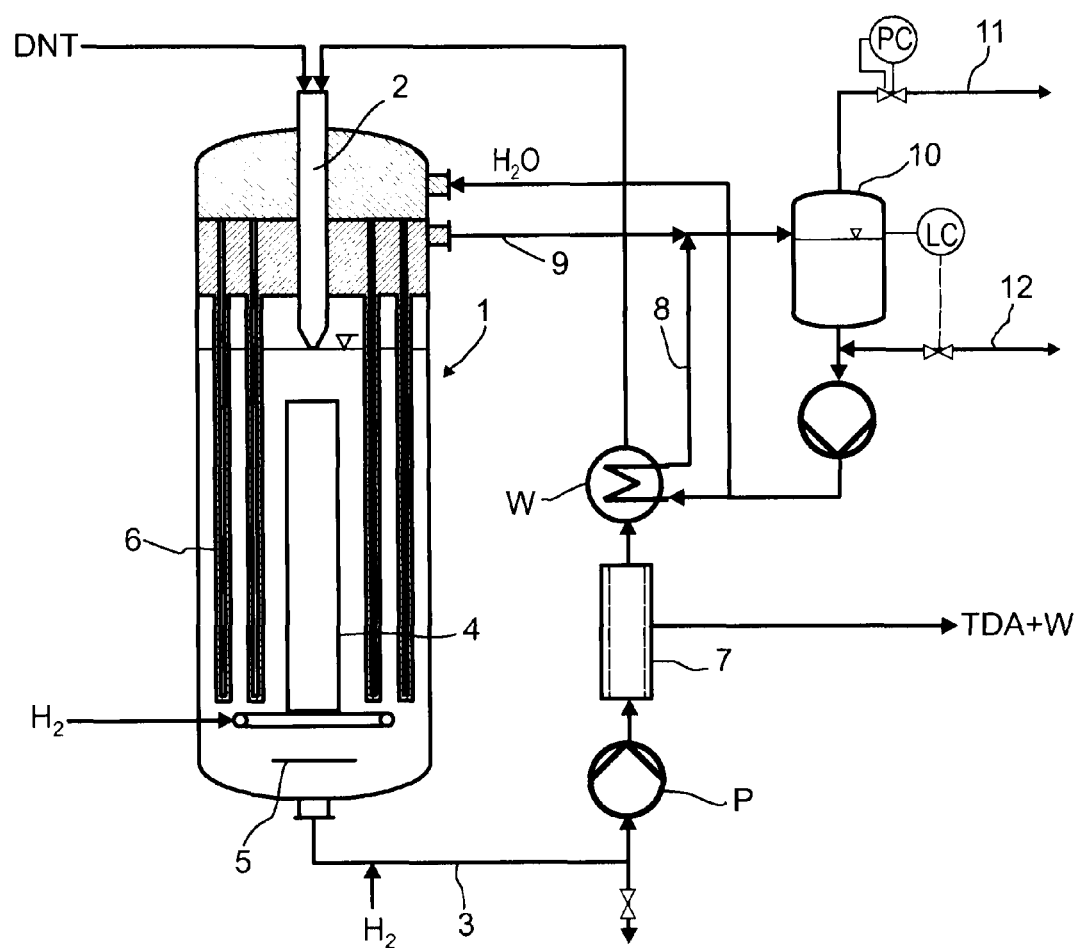

METHOD FOR PRODUCING TOLUYLENEDIAMINE BY HYDROGENATING DINITROTOLUENE

The invention relates to a process for preparing tolylenediamine by hydrogenating dinitrotoluene.

Tolylenediamine is an aromatic amine which is frequently used in industry; it is especially processed further to tolylene diisocyanate, which finds use predominantly in polyurethane preparation. Tolylenediamine is prepared by catalytically hydrogenating dinitrotoluene.

A multitude of catalysts have been developed for the above reaction, in order to achieve a maximum yield and selectivity in the reaction and furthermore to discover catalysts which are stable even at relatively high reaction temperatures.

The hydrogenation of dinitrotoluene releases a large amount of heat of reaction. The aim has therefore always been to utilize this heat of reaction, for example in the form of steam.

Document U.S. Pat. No. 5,563,296 describes a process and a reactor for preparing tolylenediamine by hydrogenating dinitrotoluene in a reactor with an external loop, wherein the heat is removed exclusively in the external loop. A disadvantage of this process is that, when steam is raised, the boiling temperature of the steam must be significantly below the reaction temperature, since the area of the external heat exchanger and the amount of liquid to be circulated otherwise become too great for an economically viable process.

The hydrogenation of dinitrotoluene is strongly exothermic. As a reactor particularly suitable for the removal of the heat of reaction, WO 00/35852 therefore proposed a reactor with internal and external loop motion, which is configured as a vertically upright apparatus, with a motive jet nozzle at the upper end thereof, through which the reaction mixture drawn off from the reactor bottom, via an external loop, is sprayed into the upper region of the reactor, and then flows into a central inserted tube which is arranged in the longitudinal direction of the reactor, flows through the latter from the top downward and flows upward again outside the inserted tube in an internal loop motion. For the removal of the heat of reaction, heat exchangers, especially Field tubes, are provided in the reactor interior, i.e. double tubes arranged vertically in the longitudinal direction of the reactor, of which the inner tube is open at the bottom and the outer tube is closed at the bottom, and within which a heat carrier, especially water, flows and removes the heat of reaction. In addition to the heat removal by means of heat exchangers arranged in the reactor interior, a heat exchanger may also be arranged in the external loop flow.

EP-A 124010 describes a bubble column for hydrogenation of dinitrotoluene compounds to the corresponding amines. The heat of reaction is removed by means of Field tubes. The aim is to raise steam with a pressure of >1 bar gage. This is based on a specific heat transfer area of 40 to 400 $m^2/m^3$ based on the reaction volume. The disadvantage of this arrangement is that, given such large cooling areas, the distance between the cooling tubes is so small that fouling and solid deposits have to be expected. Furthermore, the macroscopic mixing of the apparatus is massively disrupted.

The challenge in all of the above processes is that a low reaction temperature, i.e. a small difference between reaction temperature and steam temperature, has a positive effect on the selectivity of the reaction but leads to uneconomically large heat transfer areas.

It was therefore an object of the invention to find an economically attractive process for catalytically hydrogenating dinitrotoluene to tolylenediamine, in which the temperature level of the steam is as close as possible to the reaction temperature. The steam raised should have a pressure of ≥4 bar gage.

This object is achieved in a process for preparing tolylenediamine by hydrogenating dinitrotoluene with hydrogen in the presence of a suspended catalyst in a vertically upright reactor,
at the upper end of which is arranged a motive jet nozzle through which the reaction mixture drawn off from the reactor bottom, via an external loop, is sprayed into the upper region of the reactor and then flows into a central inserted tube which is arranged in the longitudinal direction of the reactor, flows through the latter from the top downward and flows upward again outside the inserted tube in an internal loop motion,
with a heat exchanger in the interior of the reactor, through which cooling water flows, and absorbs some of the heat of reaction as it does so,
with a feed for the dinitrotoluene at the upper end of the reactor and a feed for the hydrogen at the lower end of the reactor,
and wherein, in addition to the heat exchanger arranged in the interior of the reactor, a further heat exchanger is used in the external loop, in which water absorbs the rest of the heat of reaction by indirect heat exchange with the reaction mixture, which comprises
utilizing the heat of reaction to raise steam with a pressure of at least 4 bar gage by performing the hydrogenation of dinitrotoluene to tolylenediamine at a temperature of ≥180° C.

Preference is given to performing the hydrogenation of dinitrotoluene to tolylenediamine at a temperature of ≥185° C.

It has been found that it is possible to perform the hydrogenation of dinitrotoluene to tolylenediamine in such a way that not only a high selectivity and yield of the reaction itself is achieved, but that the heat of reaction can additionally be utilized in order to raise steam at a high pressure level, of 4 bar gauge or higher, as is typically provided in the steam lines in industrial plants. This makes it possible to feed the steam into the existing steam grid and/or to utilize it in the overall plant, proceeding from toluene through dinitrotoluene and tolylenediamine up to the preparation of tolylene diisocyanate.

Alternatively, it is also possible to provide steam at two pressure levels of 4 bar gauge or higher.

For the hydrogenation of dinitrotoluene to tolylenediamine, a multitude of catalysts have been developed, the primary objects in the development of novel catalysts having been the improvement of yield and selectivity of the reaction and the stability of the catalysts even at relatively high reaction temperatures.

Particularly suitable catalysts have been found to be those which comprise, as an active material, one or more metals selected from the group of platinum, palladium, rhodium and ruthenium, and additionally one or more further metals selected from the group of nickel, cobalt, iron and zinc, and which are applied to an inert support.

Especially advantageous are catalysts which comprise, as the active material, platinum and additionally nickel, or else catalysts which comprise palladium, nickel and iron, or catalysts which comprise palladium, nickel and cobalt.

Particularly advantageous hydrogenation catalysts are those which comprise platinum and nickel on a support in the form of an alloy with an atomic ratio of nickel to platinum in the alloy between 30:70 and 70:30.

Alloys composed of platinum and nickel with other atomic ratios are also useable in principle for the process according to the invention, but they lead, especially in the case of performance of the hydrogenation at relatively high temperatures, to low yields of TDA.

The atomic ratio of nickel to platinum, determined by means of EDXS (Energy Dispersive X-Ray Spectroscopy), is especially between 45:55 and 55:45.

The catalyst usually comprises finely crystalline metal particles of the Pt—Ni alloy of size approx. 1 to 15 nm distributed on, for example, carbon particles. In places, Ni—Pt particle agglomerates or aggregates of size 1 to 2 μm, but also isolated pure Ni or Pt particles, may occur on the support. The electron diffraction lines of the metal particles are between those of Pt and Ni, which additionally confirms alloy formation. The metal particles are usually polycrystalline, and can be characterized with a high-resolution TEM (FEG-TEM: Field Emission Gun-Transmission Electron Microscopy).

The supports used for the catalysts may be the known materials customary for this purpose. Preference is given to using activated carbon, carbon black, graphite or metal oxides, preferably hydrothermally stable metal oxides, for example $ZrO_2$, $TiO_2$. In the case of graphite, the HSAGs (High Surface Area Graphites) with a surface area of 50 to 300 $m^2/g$ are particularly preferred. Particular preference is given to the physically or chemically activated carbons or carbon blacks, such as acetylene black.

The aim of the process is to provide steam at a temperature level of ≥4 bar gage. At the same time, the reaction temperature should not be selected at too high a level in order to prevent selectivity losses as a result of side reactions (for example high boiler formation). This leads to large heat transfer areas being required. When the heat transferrer for removal of the heat of reaction is exclusively integrated into the reactor, this results in a very large reactor volume and therefore in very low space-time yields. When the heat transferrer is integrated exclusively into the external cycle, this results in a very large circulation stream, since the medium in the external heat transferrer cannot be cooled too greatly in order to provide steam at a high pressure level.

The steam can therefore only be provided in an economically viable manner when the heat is removed simultaneously in the apparatus and in the external circuit. This leads simultaneously to acceptable reactor volumes and high space-time yields.

The process is therefore preferably performed at space-time yields of greater than 150 kg of tolylenediamine per $m^3$ of sparged reactor volume and hour, especially at space-time yields of greater than 250 kg of tolylenediamine per $m^3$ of sparged reactor volume and hour.

The process is preferably performed without addition of a solvent.

The process according to the invention is performed in a reactor in which an internal and an external loop motion of the reaction mixture take place.

To this end, a motive jet nozzle is arranged in a vertically upright reactor at the upper end thereof and drives the internal loop motion, specifically by spraying the reaction mixture drawn off from the reactor bottom, which is pumped in circulation through an external loop, downward into the upper region of the reactor via the motive jet nozzle. The reaction mixture sprayed in via the motive jet nozzle flows through a central inserted tube arranged in the longitudinal direction of the reactor and flows through it from the top downward. The central inserted tube can be configured as a simple tube. Below the inserted tube, the reaction mixture turns back outside the inserted tube in an internal loop motion and flows upward again. For flow reversal, a baffle plate is preferably arranged below the inserted tube.

The concentric inserted tube in conjunction with the baffle plate stabilizes the loop flow within the reactor, i.e. the internal loop flow.

The motive jet entrains gas out of the gas space into the liquid in the form of gas bubbles up to the baffle plate. These gas bubbles ascend again in the annular space of the reactor. This internal cycle gas method provides a large gas/liquid phase interface.

A heat exchanger is arranged in the reactor interior for heat removal, through which the cooling water flows and absorbs some of the heat of reaction.

The heat exchanger arranged in the reactor interior is preferably a Field tube heat exchanger.

In one embodiment, the heat exchanger arranged in the interior of the reactor is a coiled tube heat exchanger.

In a further embodiment, the heat exchanger arranged in the interior of the reactor is a tube bundle heat exchanger.

The remainder of the heat of reaction is removed by means of a heat transferrer which is arranged in the external loop. Preference is given to using a tube bundle heat transferrer.

Steam can be generated from the heat of reaction released both in the internal and the external heat transferrer in two ways: 1) by evaporation of some of the cooling water in the cooling tubes (direct steam generation) or 2) by heating the cooling water to a pressure above the pressure of the steam to be raised, and then decompressing to the pressure level of the steam to be raised (flash evaporation). This decompression evaporates some of the cooling water, and the steam/water mixture cools down to the boiling temperature corresponding to the pressure of the steam.

Both types of evaporation can be employed both in the internal and external heat transferrer. A combination of the two evaporation types is equally possible, i.e. direct evaporation in the internal heat transferrer and flash evaporation in the external transferrer, or vice versa.

Dinitrotoluene is fed in at the upper end of the reactor, preferably into the gas phase above the liquid level in the reactor.

Advantageously, the dinitrotoluene is supplied by means of a ring distributor to homogenize the supply.

In a further embodiment, the motive jet nozzle arranged in the upper region of the reactor is configured as a two-jet nozzle, and the dinitrotoluene is passed into the reactor via an annular gap on the outer wall of the motive jet nozzle configured as a two-jet nozzle.

The inventors have recognized that it is advantageous to introduce the dinitrotoluene into the gas phase above the liquid level in the reactor; this prevents reaction product from flowing back into the feed line for dinitrotoluene and thus leading to decomposition or explosion of the dinitrotoluene. Pure dinitrotoluene has a decomposition temperature of about 260° C., but the decomposition temperature falls drastically as soon as tolylenediamine is added, down to 100° C.

It is therefore also advantageous to purge the feed line with hot water to free it of the dinitrotoluene in the event of interruptions in production or shutdowns of the plant.

The inventors have recognized that it is essential that less than 1000 ppm of dinitrotoluene accumulates in the reactor.

The hydrogen needed for the hydrogenation is fed in at the lower end of the reactor, preferably via a ring distributor.

The inventors have recognized that it is advantageous to ensure, by means of suitable measures, that the concentration of the hydrogen in the reaction mixture which flows out of the reactor bottom into the external loop does not go below 1% by volume, preferably 3% by volume, based on the total volume of the reaction mixture which flows within the external loop.

To this end, it is possible to correspondingly design the diameter of the reactor or the flow rate of the reaction mixture out of the reactor.

In a further embodiment, it is possible to ensure the minimum concentration of the hydrogen which flows out of the reactor bottom into the external loop by supplying hydrogen as close as possible to the reactor into the reaction mixture which flows out of the reactor bottom into the external loop.

In order to be able to drive the external circulation, it is necessary to install a pump which, as well as liquid, can also deliver gas and suspended solids. Up to 20% by volume of gas and 20% by weight of suspended solids should be pumpable.

The steam raised can be fed into an existing steam grid of the site of the plant, or be utilized directly in the overall plant, proceeding from toluene through dinitrotoluene and tolylenediamine up to the preparation of tolylene diisocyanate.

The steam at a level of at least 4 bar gage raised by the process according to the invention can be used at many points within and outside the tolylene diisocyanate (TDI) process. Some possible uses are listed hereinafter, but this is not intended to mean that the use of the steam raised is restricted only to these possibilities.

The steam can be utilized for heat or energy supply within the overall TDI complex, in which the tolylenediamine (TDA) stage constitutes only one part. More particularly, it is suitable for use in one or more of the process stages listed below:
  in the evaporation or distillation for concentration of acids at the nitration (dinitrotoluene) stage,
  in the water removal in the evaporator of the TDA/water distillation,
  in the removal of the TDA from high-boiling residue (distillation or evaporation),
  in the TDI synthesis stage in the phosgene or HCl stripping,
  in the heating of the reactor or of the reaction column for phosgenation of TDA,
  in the evaporator in the TDI distillation,
  when evaporating off the solvent used in the phosgenation,
  and in the operation of vacuum jets (generation of vacuum by decompressing the steam) in the overall TDI complex.

Furthermore, the steam can be used in one or more of the areas listed below:
  for evaporating off solvents from process wastewater,
  for generating cold temperatures by means of absorption refrigerators or steam jet coolers,
  for generating vacuum in the case of decompression in ejectors,
  for generating power as an energy or heat source for thermal power processes (direct decompression in a turbine or ORC or Kalina cycles),
  for heating pipelines, apparatus, vessels or tanks,
  and for heating buildings.

In addition, the steam can also be fed into an available steam grid at the site of the plant.

The invention is illustrated in detail below by an example and a FIGURE.

The sole FIGURE, FIG. 1, shows the schematic diagram of a plant for performing the process according to the invention.

The reactor 1 is equipped with a motive jet nozzle 2 directed downward in the upper region thereof, through which the reaction mixture is sprayed into the reactor via an external loop 3. Below the motive jet nozzle 2 is arranged a central inserted tube 4 arranged in the longitudinal direction of the reactor, and below the inserted tube 4 a baffle plate 5. In the interior of the reactor 1 is a Field tube heat exchanger 6. Dinitrotoluene, DNT, in the preferred variant shown in the FIGURE, is fed via an annular gap on the outer wall of the motive jet nozzle 2 configured as a two-jet nozzle into the reactor 1 into the gas space above the liquid level.

Hydrogen, $H_2$, is sprayed into the lower region of the reactor 1, in the preferred variant shown in the FIGURE via a ring distributor 7, and additionally into the external loop 3, close to the draw of the reaction mixture out of the reactor bottom. Within the external loop, the reaction mixture is passed through a pump P which is designed such that it can deliver up to 20% by volume of gas, in the preferred embodiment shown in the FIGURE through a crossflow filter 7 for catalyst removal. The reaction mixture is subsequently passed through a heat exchanger W which is arranged in the external loop and is preferably configured as a tube bundle heat exchanger. Steam is drawn off via line 8 from the heat exchanger W arranged in the external loop, and combined with steam via line 9 from the Field tubes, which are fed with water, $H_2O$, fed to a separator 10 and drawn off as steam at 4 bar gage via line 11. Via line 12 a part stream of the condensate is drawn off.

EXAMPLE

In a plant as shown schematically in FIG. 1, dinitrotoluene was hydrogenated to tolylenediamine in a reactor with an external loop 3 with liquid volume 170 l (total volume of reactor 1+external loop 3) at 180° C. and 25 bar gage. In the external loop 3, 4.5 m$^3$/h of liquid were circulated with a pump P which can also pump gas bubbles present and suspended solid particles. In the reactor 1, a gas content of approx. 15% by volume was established. The hydrogenation bath comprised 2% by weight of a suspended catalyst with 3% by weight of Pt and 1% by weight of Ni on carbon supports. For catalyst retention, a crossflow filter 7 with a membrane of pore size 1000 nm was used. At the lower outlet of the reactor 1, a small amount of hydrogen was fed into the outer loop 3.

A feed stream of 62 kg/h of DNT was fed in. This DNT was converted fully in the reactor 1. This gave rise to a space-time yield of 245 kg of TDA/(m$^3$/h).

The selectivity for TDA was 98.69%, that for high boilers 1.25% and that for low boilers 0.06%. In the reactor 1, heat of reaction of 106 kW was released.

If steam at a pressure level of 4 bar gage and at a temperature of 155° C. is now to be raised, in accordance with the invention, some of the heat of reaction is removed in reactor 1 under virtually isothermal conditions, and the remainder of the heat of reaction in the external loop 4.

For the heat removal in the interior of the reactor 1, a Field tube heat exchanger 6 is provided in the annular space around the inserted tube 4, and a specific heat exchange area of 15 m$^2$/m$^3$ is assumed. As a result, only a small portion of the cross-sectional area of the reactor 1 is blocked, and the flow in the reactor interior is not hindered too greatly. The heat exchange area of the Field tube heat exchanger 6 is thus 2.55 m$^2$, and a total of 70 kW of heat of reaction is removed at a heat transfer coefficient of 1100 W/(m$^2$/K).

The remaining 36 kW of heat of reaction are circulated by means of the external heat exchanger W. At a specific heat capacity of the hydrogenation bath of 3.3 kJ/(kg/K), the liquid cools from 180° C. upstream of the external heat exchanger W to 171° C. downstream of the external heat exchanger W. For heat removal, a mean logarithmic temperature difference of 20 K is available. When the basis is a heat transfer coefficient of 1000 W/(m$^2$/K), a heat transfer area of 1.80 m$^2$ is required. The external heat exchanger 6 used is a tube bundle heat exchanger.

If, for comparison, all of the heat of reaction were removed in the interior of the reactor 1, a specific heat transfer area of 23 m$^2$/m$^3$ (i.e. 3.9 m$^2$ absolute) would be required. This would block a large portion of the cross-sectional area of the reactor 1 with heat exchanger tubes, and the risk of fouling in the reactor interior owing to excessively decelerated flow would be great.

If, instead, all of the heat of reaction is removed by means of the external heat exchanger W, steam could no longer be generated at a temperature level of 155° C. at the given circulation flow of 4.5 m$^3$/h, since the temperature of the hydrogenation bath pumped in circulation at the outlet of the external heat exchanger would be below 155° C. in this case.

The invention claimed is:

1. A process for preparing tolylenediamine by hydrogenating dinitrotoluene with hydrogen in the presence of a suspended catalyst
    in a vertically upright reactor,
    at the upper end of which is arranged a motive jet nozzle through which the reaction mixture drawn off from the reactor bottom, via an external loop, is sprayed into the upper region of the reactor and then flows into a central inserted tube which is arranged in the longitudinal direction of the reactor, flows through the latter from the top downward and flows upward again outside the inserted tube in an internal loop motion,
    with a heat exchanger in the interior of the reactor, through which cooling water flows, and absorbs some of the heat of reaction as it does so,
    with a feed for the dinitrotoluene at the upper end of the reactor and a feed for the hydrogen at the lower end of the reactor,
    and wherein, in addition to the heat exchanger arranged in the interior of the reactor, a further heat exchanger is used in the external loop, in which water absorbs the rest of the heat of reaction by indirect heat exchange with the reaction mixture,
    which comprises
    utilizing the heat of reaction to raise steam with a pressure of at least 4 bar gauge by performing the hydrogenation of dinitrotoluene to tolylenediamine at a temperature of greater than or equal to 180° C., and wherein the dinitrotoluene is supplied to the reactor into the gas phase above the liquid level or wherein the motive jet nozzle is configured as a two jet nozzle, and wherein the dinitrotoluene is supplied to the motive jet nozzle.

2. The process according to claim 1, wherein the hydrogenation of dinitrotoluene to tolylenediamine is performed at a temperature of greater than or equal to 185° C.

3. The process according to claim 1, wherein the catalyst comprises, as an active material, a metal selected from the group consisting of platinum, palladium, rhodium and ruthenium, together with one or more further metals selected from the group consisting of nickel, cobalt, iron, zinc, which are applied to an inert support.

4. The process according to claim 3, wherein the active material of the catalyst comprises platinum and nickel, or palladium, nickel and cobalt, or palladium, nickel and iron.

5. The process according to claim 1, wherein the heat exchanger arranged in the reactor interior is a Field tube heat exchanger.

6. The process according to claim 1, wherein the heat exchanger arranged in the reactor interior is a coiled tube heat exchanger.

7. The process according to claim 1, wherein the heat exchanger is a tube bundle heat exchanger.

8. The process according to claim 1, wherein the heat exchanger arranged in the external loop is a tube bundle heat exchanger.

9. The process according to claim 1, wherein the dinitrotoluene is supplied by means of a ring distributor.

10. The process according to claim 9, wherein it is ensured that the concentration of the hydrogen in the reaction mixture which flows out of the reactor bottom into the external loop does not go below 1% by volume.

11. The process according to claim 10, wherein the minimum concentration of the hydrogen in the reaction mixture which flows out of the reaction bottoms into the external loop is ensured by correspondingly designing the diameter of the reactor or the flow rate of the reaction mixture out of the reactor bottom.

12. The process according to claim 10, wherein the minimum concentration of the hydrogen in the reaction mixture which flows out of the reactor bottom into the external loop is ensured by supplying hydrogen as close as possible to the reactor into the reaction mixture which flows out of the reactor bottom into the external loop.

13. The process according to claim 1, wherein it is ensured that the concentration of the hydrogen in the reaction mixture which flows out of the reactor bottom into the external loop does not go below 3% by volume.

* * * * *